United States Patent
Engle

(10) Patent No.: US 8,226,599 B2
(45) Date of Patent: Jul. 24, 2012

(54) ULTRASONIC METHOD FOR ESTABLISHING AND MAINTAINING A LIQUID SUSPENSION DELIVERY SYSTEM THAT PREVENTS THE DISPERSED PARTICLES FROM PRECIPITATING OUT OF SUSPENSION

(75) Inventor: Robb W. Engle, Kingston, NY (US)

(73) Assignee: Sono-Tek Corporation, Milton, NY (US)

( * ) Notice: Subject to any disclaimer, the term of this patent is extended or adjusted under 35 U.S.C. 154(b) by 176 days.

(21) Appl. No.: 12/098,679

(22) Filed: Apr. 7, 2008

(65) Prior Publication Data

US 2009/0254020 A1 Oct. 8, 2009

Related U.S. Application Data

(60) Provisional application No. 61/041,853, filed on Apr. 2, 2008.

(51) Int. Cl.
*A61M 37/00* (2006.01)
(52) U.S. Cl. .......................................... 604/82; 604/22
(58) Field of Classification Search .................. 604/82, 604/92, 187, 22; 239/102.1–102.2
See application file for complete search history.

(56) References Cited

U.S. PATENT DOCUMENTS

| | | | | |
|---|---|---|---|---|
| 4,167,880 | A * | 9/1979 | George | 73/644 |
| 5,324,297 | A * | 6/1994 | Hood et al. | 606/99 |
| 5,516,043 | A * | 5/1996 | Manna et al. | 239/102.2 |
| 6,254,587 | B1 * | 7/2001 | Christ et al. | 604/521 |
| 6,623,444 | B2 * | 9/2003 | Babaev | 604/22 |
| 6,723,064 | B2 * | 4/2004 | Babaev | 604/22 |
| 6,776,352 | B2 * | 8/2004 | Jameson | 239/1 |
| 2003/0125645 | A1 * | 7/2003 | Rabiner et al. | 601/2 |
| 2005/0101942 | A1 * | 5/2005 | Gillis et al. | 604/891.1 |
| 2006/0184102 | A1 * | 8/2006 | Trombley et al. | 604/82 |
| 2007/0003584 | A1 * | 1/2007 | Anderson | 424/401 |
| 2009/0187136 | A1 * | 7/2009 | Babaev | 604/22 |

* cited by examiner

*Primary Examiner* — Kevin C Sirmons
*Assistant Examiner* — Brandy C Scott
(74) *Attorney, Agent, or Firm* — Baker & Hostetler LLP

(57) ABSTRACT

The present invention relates generally to a method and apparatus for applying wave energy of an ultrasonic frequency to agitate particles in a sample. The agitated sample is then delivered via a syringe or a resonating syringe plunger attachment of an applicator. More particularly, the present invention relates to establishing and maintaining a liquid suspension delivery system that prevents dispersed particles from precipitating out of suspension while the sample is delivered through to various applicators, such as resonating syringe plungers.

13 Claims, 4 Drawing Sheets

ULTRASONIC METHOD FOR ESTABLISHING AND MAINTAINING A LIQUID SUSPENSION DELIVERY SYSTEM THAT PREVENTS THE DISPERSED PARTICLES FROM PRECIPITATING OUT OF SUSPENSION

CROSS-REFERENCE TO RELATED APPLICATIONS

This application is related to U.S. Provisional Patent Application Ser. No. 61/041,853, titled "Ultrasonic Method for Establishing and Maintaining a Liquid Suspension Delivery System That Prevents The Dispersed Particles From Precipitating Out of Suspension," filed Apr. 2, 2008, the disclosures of each which are hereby incorporated by reference in their entirety.

FIELD OF THE INVENTION

The present invention relates generally to a method and apparatus for applying ultrasonic frequency wave energy to agitate particles in a sample. More particularly, the present invention relates to establishing and maintaining a liquid suspension delivery system that prevents dispersed particles from precipitating out of suspension while delivering the material to various devices, such as resonating syringe plungers and syringes.

BACKGROUND OF THE INVENTION

Scientists, technicians and others often have problems delivering precise proportions of materials (solutes) in a suspension liquid to a surface. They have discovered inconsistent mixture ratios bring about high waste when solutes come out of suspension. For example, a suspension in a barrel of a syringe applicator comes out of suspension leaving unusable and undelivered material in the syringe. The scientist will have to "waste" or dispose of this left over material. The material may be hazardous and thus time consuming and costly to dispose of properly.

Another problem faced with solution delivery mechanisms is uneven distribution of materials in the solution. For example, a 10 cc solution in a delivery apparatus may have a higher concentration of solutes in the lower elevations of a solution sample and a lesser concentration of solutes in the upper elevations of the solution sample. Therefore, as the suspension is delivered or applied its concentration or ratio of solutes to liquid varies as it is delivered or applied to a surface.

A common technique to produce a solution is to utilize an ultrasonic mixing system and uses wave energy at the upper threshold of human hearing, which starts at 20,000 hertz to mix and speed dissolution. This is achieved by breaking the molecular bonds in a solute and go into a solution. Additionally, this technique may provide energy needed for certain chemical reactions to start.

A problem with current delivery techniques is the precipitation of suspended particles or coming out of solution immediately before the solution is delivered. This occurs when the agitation or mixing is stopped and the solution is moved from the mixing or staging area to the applicator. Therefore, what is needed is a system and a methodology to keep the particles suspended as they are delivered.

SUMMARY OF THE INVENTION

The present invention relates generally to a method and apparatus for applying sound energy to agitate particles in a sample with an ultrasonic resonating syringe plungers that pushes a liquid solution towards said syringe's exit. Therefore, a solution is both agitated and delivered from within the syringe. More particularly, the present invention relates to establishing and/or maintaining a liquid suspension, in a delivery system that prevents dispersed particles from precipitating out of suspension while the sample is delivered to various types of applicators.

An embodiment has a syringe applicator devise composed of a glass and/or steel outer body with a titanium and Teflon resonating syringe plunger. The solution is extruded out by engaging the resonating syringe plunger. The resonating syringe plunger incorporates resonant transducers that operate in ultra-sonic frequency range of 20,000 to 120,000 Hz. to mix and agitate the solution.

In an embodiment, an ultrasonic suspension delivery device is disclosed. It comprises a solution delivery device with an ultrasonic pushing assembly with a horn agitator assembly and at least one power connector to receive power from an ultrasonic energy source. It has a barrel with at least one liquid intake and outtake port; and said barrel with an additional opening permitting said solution delivery device ingress and egress, while hydro dynamically sealing ultrasonic pushing assembly from said horn agitator assembly.

In an additional embodiment, portions of the device are made out of titanium or stainless steel. For example, the ultrasonic pushing assembly and/or the horn agitator assembly. The horn agitator can also be made from a ceramic material.

In yet another embodiment, the ultrasonic energy source operates in the frequency range of 20,000 to 120,000 Hz. providing a multitude of options to find an optimal agitation frequency of a solution.

In an embodiment, the barrel is made out of glass or plastic, permitting disposability, interchangeability and the opportunity to use the least reactive material to hold the solution.

In an additional embodiment the barrel can accommodate a needle or a cannula delivery system. Thus it can be adapted to various uses, depending on the requirements. For example, when coating a surface of a silicon wafer, the user may wish to use a cannula with an atomizing sprayer.

In an embodiment, the device can use a SubMiniature version A (SMA) coaxial connector or a twisted pair cable with a Euro style M12 connector instead of being hardwired to the ultrasonic power source, thus permitting transducer interchangeability. One device can be used while a second one is being cleaned or serviced.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE INVENTION

Figure 1:
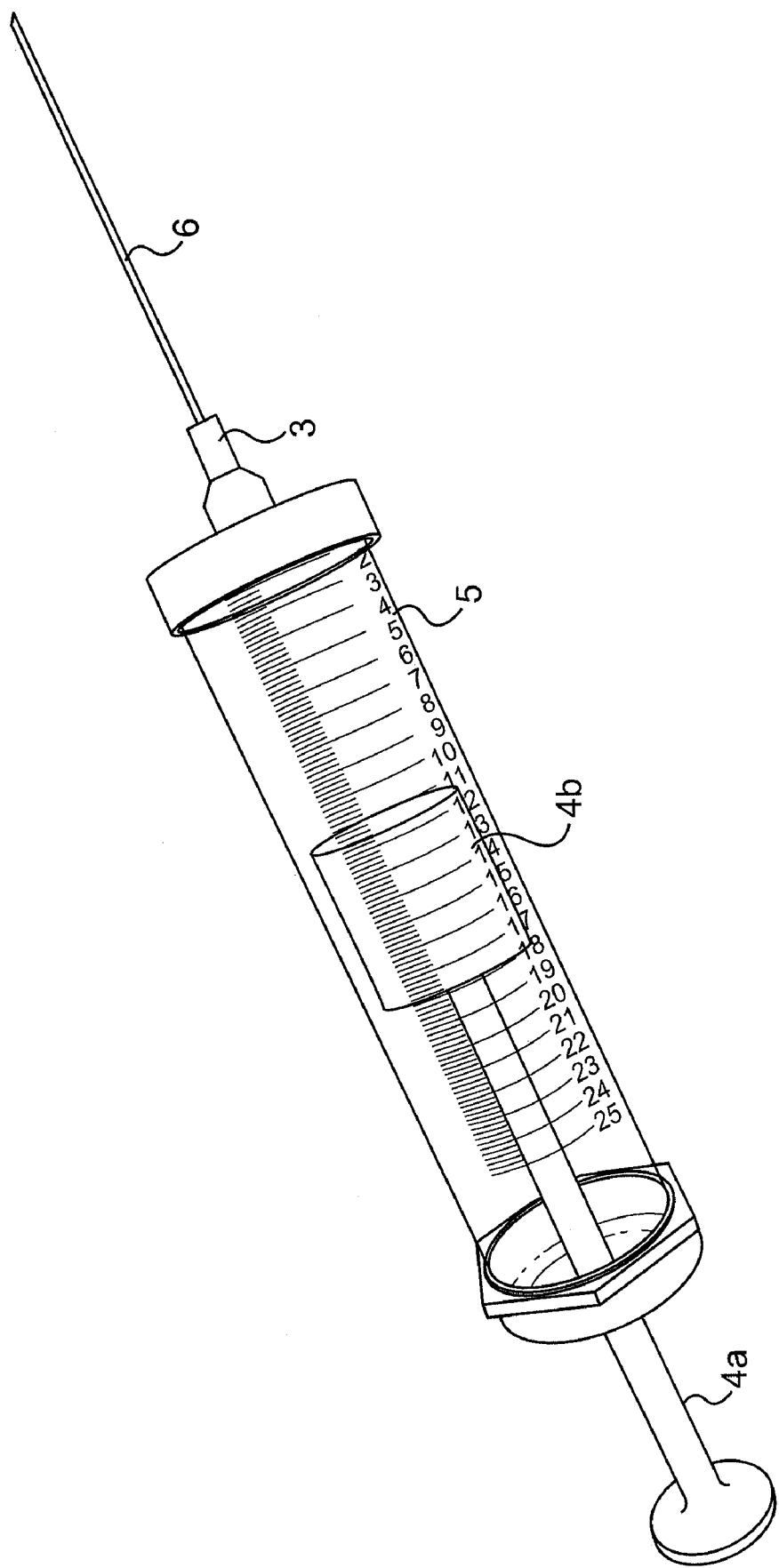
FIG. 1 shows a simple hand-powered piston syringe.
Figure 2:
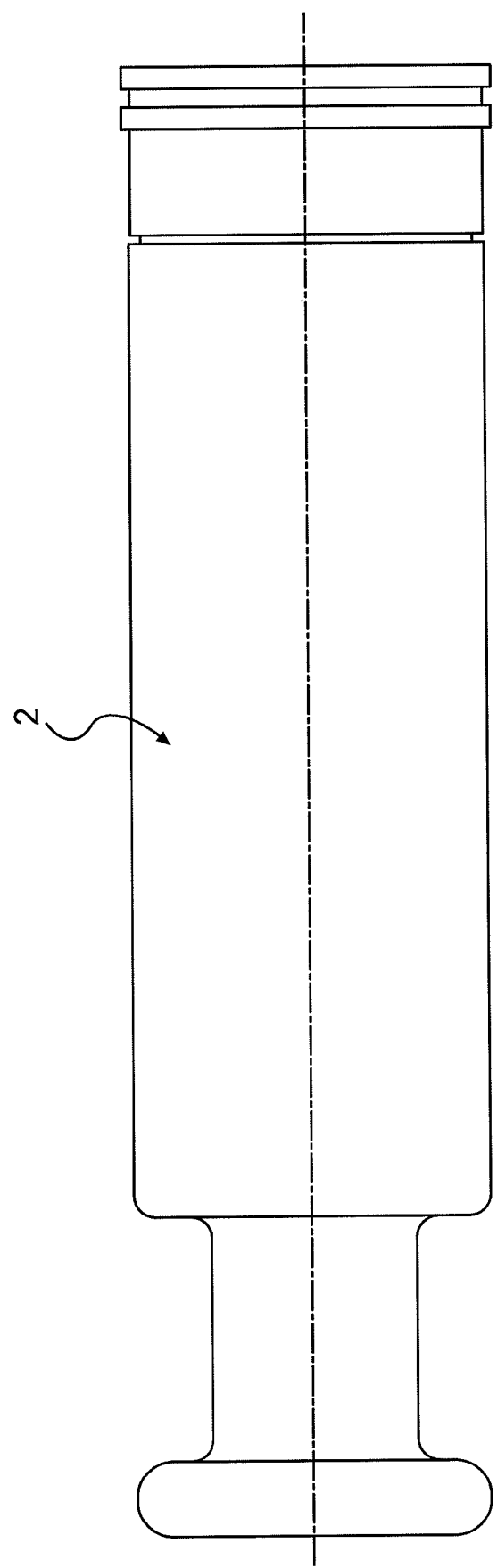
FIG. 2 illustrates a simple piston pump plunger component of an ordinary syringe.
Figure 3:
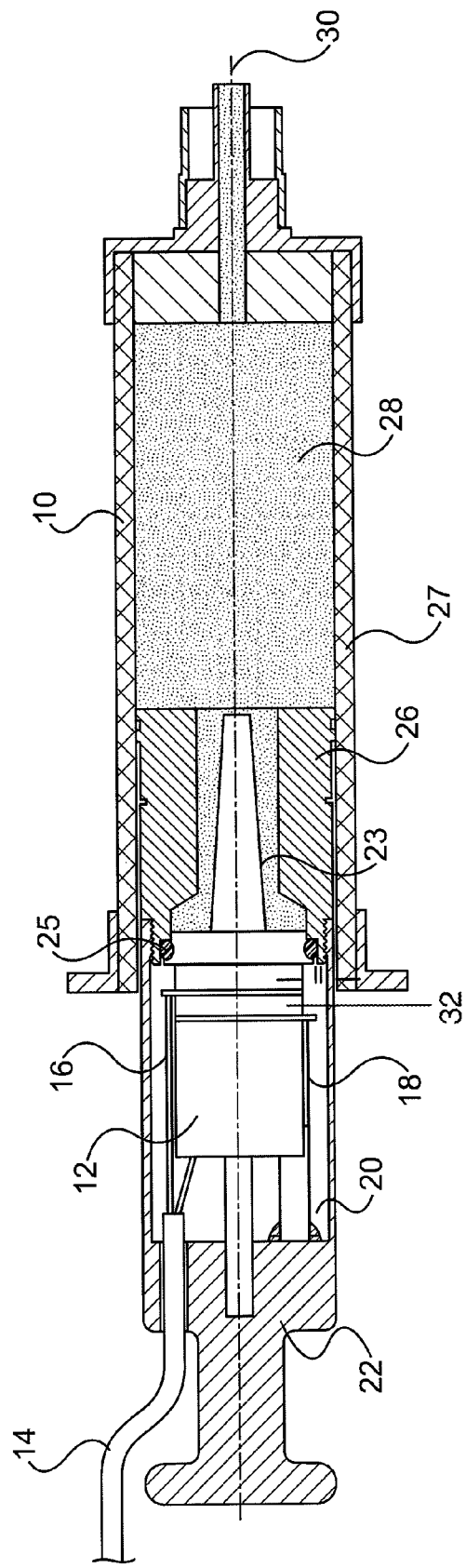
FIG. 3 is a side perspective view of the ultrasonic suspension syringe plunger to be used in combination with a syringe vessel.
Figure 4:
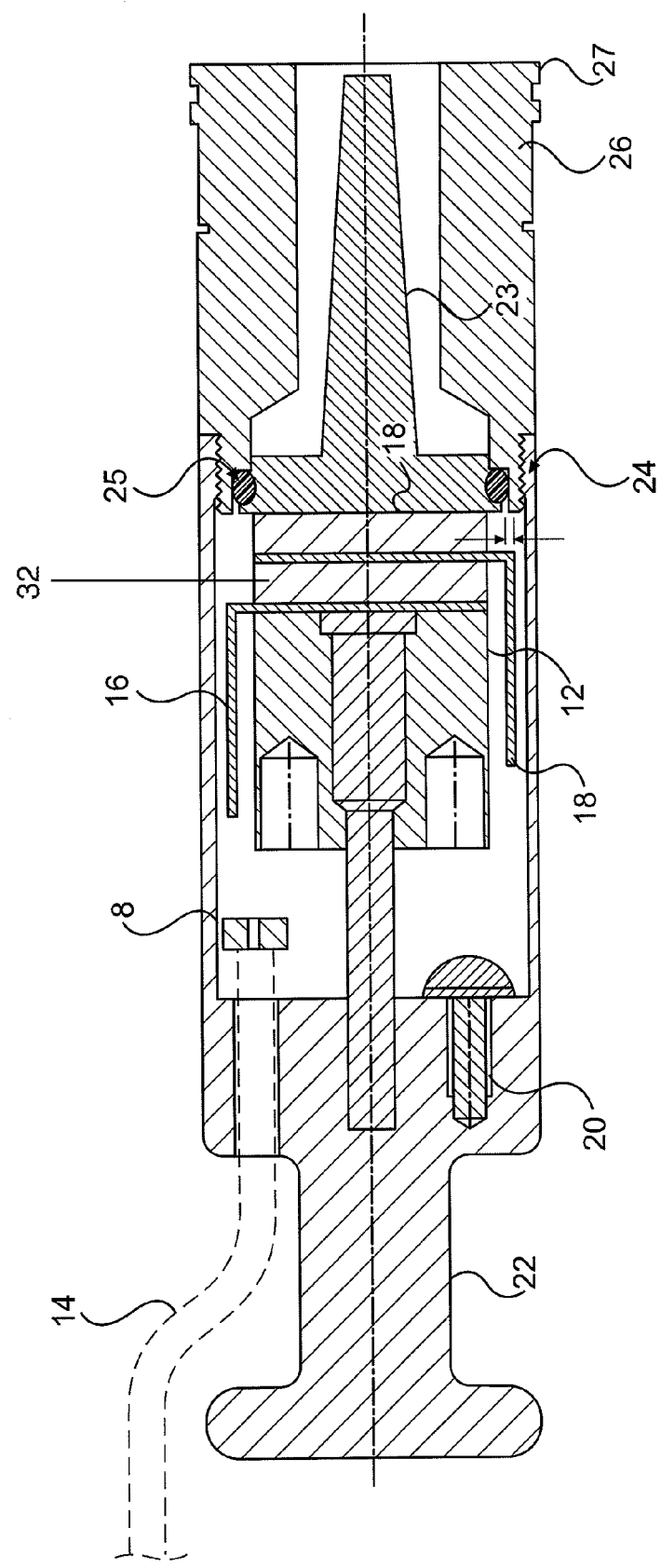
FIG. 4 is a side perspective view of the ultrasonic piston pump plunger.

The present invention relates generally to a method and apparatus for applying wave energy of an ultrasonic frequency to agitate particles in a sample. The agitated sample is then delivered from the syringe vessel to the target applicator, usually a resonating syringe plunger. More particularly, the present invention relates to establishing and maintaining a liquid suspension delivery system that prevents dispersed particles from precipitating out of suspension while the sample is delivered to various applicators.

A simple hand-powered piston syringe pump is illustrated in FIG. 1, consisting of a lower piston plunger 4*a* and an upper piston plunger 4*b* that can be pulled and pushed inside a cylindrical tube 5 (the barrel), which has a small hole 3 on one end. The syringe draws a liquid in and then extrude it out through the small hole 3. A needle 6 or cannula delivery mechanism is affixed at the top of the cylindrical tube 5. FIG. 2 illustrates another type of simple piston pump plunger 2.

To deliver a suspension liquid with this type of delivery systems, the user would first prepare a solution and draw it up through the small hole 3 by retracting the lower plunger 4*a* and an upper plunger 4*b* assembly. Once the desirable amount of suspension liquid is in the cylindrical tube 5, the user can then push the lower plunger 4*a* and an upper plunger 4*b* assembly into the cylindrical tube 5 forcing the liquid out the small hole 3. Small hole 3 can have a needle 6 or an atomizing spraying assembly (not shown) affixed to the cylindrical tube 5.

A first embodiment is shown in FIG. 3. A cylindrical tube (barrel) 10 is made out of glass. It should be noted that the cylindrical tube (barrel) 10 can be made from any hard material, such as titanium, aluminum, stainless steel, plastic or any material with no or little reactive properties. Power is connected to the ultrasonic resonating syringe plungers 12 by power cable 14 to a negative terminal 16 and a positive terminal 18. The ultrasonic resonating syringe plungers 12 employ high frequency sound waves, those beyond the range of human hearing. It has one or more piezoelectric transducers 32 to convert electrical energy into mechanical energy. The piezoelectric transducers 32 receive electrical input in the form of a high frequency signal from a power generator and convert that into vibratory motion at the same frequency.

The resonating syringe plungers are configured such that excitation of the piezoelectric transducers creates a transverse standing wave somewhere along the length of the ultrasonic resonating syringe plungers 12. For ultrasonic energy to be effective for atomization the atomizing should take place at an anti-node. The ultrasonic resonating syringe plungers 12 is selected such that an anti-node is located within itself or within the horn agitator 23. For example, the anti-node of the standing wave can be located at the base of horn agitator 23, as shown by surface 18 of FIG. 4. causing the horn agitator 23 to vibrate and agitate the solution. The anti-node's location can be adjusted by frequency selection to accommodate the characteristics of the solute and of the suspension liquid. For example, the user may wish to place the anti-node at the midpoint of the horn agitator 23. This can be accomplished by frequency selection or selecting a different length for the ultrasonic resonating syringe plungers 12, or both.

In general, high frequency resonating syringe plungers are smaller, create smaller drops, and consequently have smaller maximum flow capacity than resonating syringe plungers that operate at lower frequencies. The speed of sound in air is 340 m/s and using a 34,000 Hz. acoustic signal, the wavelength of one sound wave is 340 m/s divided by 34,000, which is equal to 10 millimeters. A half-wave would be 5 millimeters. Therefore the length of the ultrasonic resonating syringe plunger's 12 length should be 5 millimeters. A 68,000 Hz. would have a wavelength of 5 millimeters and a half wavelength of 2.5 millimeters. The above examples were done for air at sea level and values will vary greatly with differing liquids.

It should be noted that the ultrasonic resonating syringe plungers 12 is optimally composed of titanium. Titanium is chosen due to its high tensile strength to density ratio, its high corrosion resistance, and its ability to withstand moderately high temperatures without creeping. Any other material with the similar characteristics as titanium may, also be chosen to become ultrasonic resonating syringe plungers 12.

An grounding location is provided by ground screw 20. The rear of the plunger 22 does not necessarily have to be made of titanium, for example, it can be nylon, Teflon or any other hard material that be affixed to the ultrasonic resonating syringe plungers 12. The plunger front 26 which is affixed to the plunger assembly 12 via threads and may be further sealed with an epoxy. The plunger front 26 can be made of Teflon, nylon or any other material that will not react with the liquid solution 28. An o-ring 25 further ensures a seal between the plunger front 26 and the ultrasonic resonating syringe plungers 12. A liquid seal 27 is made by shaping the plunger front 26 and its positioning against the cylindrical tube (barrel) 10 producing a dynamic seal. The suspension liquid 28 is drawn into the ultrasonic syringe and is extruded through the opening 30.

In operation, a low power alternating current (AC) is applied to the ultrasonic resonating syringe plungers 12 causing a transducer to become excited. The transducer is coupled to the transducer horn agitator 23 and begins to vibrate and agitate the solution 28. The energy for the transducers is supplied by an ultrasonic generator (not shown).

Referring to FIG. 4 which shows an additional embodiment, the resonating syringe plunger power cable 14 terminates with at a SubMiniature version A (SMA) 8 coaxial connector or any other efficient coaxial or twisted pair connector, such as or a twisted pair cable with a Euro style M12 connector. The ultrasonic resonating syringe plungers 12 has the matching SMA connector on it allowing the present invention to be connected to a ultrasonic generator via interchangeable coaxial cable facilitating uncomplicated swapping of transducers and ultrasonic generators.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

The invention claimed is:

1. An ultrasonic suspension delivery device, comprising: a barrel including a proximal opening and a distal opening coupled to a delivery mechanism; and an ultrasonic resonating syringe plunger, slidingly displaceable within the barrel for pushing a liquid toward the distal opening of the barrel, including: a front body including a bore extending completely therethrough, and a seal, disposed along the outer circumference of the distal end, to engage the inner surface of the barrel, a rear body including a bore extending partially therethrough, a proximal end having a transverse plunger surface, and a distal end attached to the proximal end of the front body, a transducer disposed within the bore of the rear body, a horn agitator, disposed within the bore of the front body, rigidly coupled to the transducer and resiliently coupled to the front body, and at least one power connector, coupled to the transducer, to receive power from an ultrasonic energy source.

2. The ultrasonic suspension delivery in claim 1, wherein the front body and the rear body of the ultrasonic resonating syringe plunger are made from titanium.

3. The ultrasonic suspension delivery in claim 1, wherein the front body and the rear body of the ultrasonic resonating syringe plunger are made from stainless steel.

4. The ultrasonic suspension delivery in claim 1, wherein said horn agitator is made from titanium.

5. The ultrasonic suspension delivery in claim 1, wherein said ultrasonic energy source operates in the frequency range of 20,000 to 120,000 Hz.

6. The ultrasonic suspension delivery in claim 1, wherein said barrel is made out of glass.

7. The ultrasonic suspension delivery in claim 1, wherein said barrel is made out of plastic.

8. The ultrasonic suspension delivery in claim 1, wherein the delivery mechanism is a needle or a cannula.

9. The ultrasonic suspension delivery in claim 1, wherein said at least one power connector is a SubMiniature version A (SMA) coaxial connector.

10. The ultrasonic suspension delivery in claim 1, wherein said at least one power connector is a coaxial connector.

11. The ultrasonic suspension delivery in claim 1, wherein the horn agitator is resiliently coupled to the front body using an O-ring.

12. The ultrasonic suspension delivery in claim 1, wherein, in operation, the transducer generates a standing wave that has an anti-node located at the proximal base of the horn agitator.

13. The ultrasonic suspension delivery in claim 1, wherein, in operation, the transducer generates a standing wave that has an anti-node located at the midpoint of the horn agitator.

* * * * *